United States Patent
Pu et al.

(10) Patent No.: US 8,586,948 B2
(45) Date of Patent: Nov. 19, 2013

(54) PARTICLE BEAM IRRADIATION APPARATUS AND PARTICLE BEAM THERAPY SYSTEM

(75) Inventors: Yuehu Pu, Chiyoda (JP); Hisashi Harada, Chiyoda (JP); Taizo Honda, Chiyoda (JP)

(73) Assignee: Mitsubishi Electric Corporation, Chiyoda-Ku, Tokyo (JP)

( * ) Notice: Subject to any disclaimer, the term of this patent is extended or adjusted under 35 U.S.C. 154(b) by 0 days.

(21) Appl. No.: 13/696,736

(22) PCT Filed: Jun. 22, 2011

(86) PCT No.: PCT/JP2011/064271
§ 371 (c)(1),
(2), (4) Date: Nov. 7, 2012

(87) PCT Pub. No.: WO2012/008274
PCT Pub. Date: Jan. 19, 2012

(65) Prior Publication Data
US 2013/0053617 A1 Feb. 28, 2013

(30) Foreign Application Priority Data
Jul. 15, 2010 (JP) .................................. 2010-160538

(51) Int. Cl.
*G21K 5/04* (2006.01)
(52) U.S. Cl.
USPC .................. 250/492.1; 250/491.1; 250/492.3; 600/1
(58) Field of Classification Search
USPC ............ 250/491.1, 492.1, 492.3, 396 R, 397; 600/1
See application file for complete search history.

(56) References Cited

U.S. PATENT DOCUMENTS 7,378,672 B2    5/2008  Harada
2004/0037390 A1*  2/2004  Mihara et al. ................... 378/65
(Continued)

FOREIGN PATENT DOCUMENTS

| JP | 10-033697 A | 2/1998 |
| JP | 11-244401 A | 9/1999 |

(Continued)

OTHER PUBLICATIONS

International Search Report (PCT/ISA/210) issued on Sep. 13, 2011, by the Japanese Patent Office as the International Searching Authority for International Application No. PCT/JP2011/064271.

(Continued)

*Primary Examiner* — Nicole Ippolito
(74) *Attorney, Agent, or Firm* — Buchanan Ingersoll & Rooney PC

(57) ABSTRACT

A particle beam irradiation apparatus comprises a particle beam shielding member which shields a part of a particle beam which is scanned, a prompt signal detector which detects a prompt signal which is generated when the particle beam which is scanned collides with the particle beam shielding member and a signal comparison device which predicts and obtains a generation pattern of a prompt signal which is generated with a predetermined scanning pattern and stores as a signal time pattern for comparison, wherein the signal comparison device detects an abnormality of scanning of a particle beam or the particle beam shielding member by comparing a detected signal time pattern which is a time pattern of a signal which is detected by the prompt signal detector to a signal time pattern for comparison which is stored.

8 Claims, 15 Drawing Sheets

(56) References Cited

U.S. PATENT DOCUMENTS

2009/0161818 A1 6/2009 Sakurai et al.
2011/0108737 A1 5/2011 Pu et al.
2011/0204262 A1 8/2011 Pu et al.

FOREIGN PATENT DOCUMENTS

| JP | 2002-191709 A | 7/2002 |
| JP | 2003-310590 A | 11/2003 |
| JP | 2007-319439 A | 12/2007 |
| JP | 2009-148494 A | 7/2009 |
| JP | 2009-261634 A | 11/2009 |

OTHER PUBLICATIONS

Written Opinion (PCT/ISA/237) issued on Sep. 13, 2011, by the Japanese Patent Office as the International Searching Authority for International Application No. PCT/JP2011/064271.

Komori et al., "Optimization of Spiral-Wobbler System for Heavy-Ion Radiotherapy", Japanese Journal of Applied Physics, 2004 (month unknown), pp. 6463-6467, vol. 43, No. 9A.

\* cited by examiner

PARTICLE BEAM IRRADIATION APPARATUS AND PARTICLE BEAM THERAPY SYSTEM

TECHNICAL FIELD

The present invention relates to a particle beam irradiation apparatus for irradiating a particle beam in accordance with the three-dimensional shape of a diseased site, which is applied to a particle beam therapy system that performs therapy by irradiating a particle beam onto a diseased site such as a tumor.

BACKGROUND ART

In a therapy method based on a particle beam, a high-energy particle beam such as a proton beam or a carbon beam, which is accelerated up to 70% of the light speed, is utilized. These high-energy particle beams have the following features when irradiated into a body. Firstly, almost all of irradiated particles stop at a position of the depth proportional to the 1.7th power of the charged particle energy. Secondly, the density (referred to as a dose) of energy, which is given to the path through which an irradiated particle passes until it stops in a body, becomes maximum at a position where the particle beam stops. A distinctive deep dose distribution curve formed along a path through which a particle beam passes is referred to as a Bragg curve and the position where the dose value becomes maximum is referred to as a Bragg peak.

In a particle beam irradiation system utilizing the irradiation field forming method, which is frequently used and referred as the two-dimensional irradiation method, first, a particle beam is spread laterally so as to form a uniform lateral irradiation field, then, by using a patient collimator or a multi-leaf collimator, the irradiation field is formed in accordance with a shape of an affected part. Further, in order to conform the maximum depth position which is a position where a particle beam stops in a body (a position of Bragg peak) to the vicinity of an edge of an affected part regardless of a lateral position, a particle beam is made to pass through an energy compensation filter which is made for each patient (referred as a patient bolus or Bolus). Further, by using an apparatus called a ridge filter, the width of Bragg peak is spread so as to cover whole of the patient's depth width. By performing the above-mentioned, in a patient's volume, substantially uniform dose distribution can be formed.

A method for spread of a particle beam in a lateral direction includes a method using a scattering member, a method using a wobbler electromagnet, etc. A wobbler method using a wobbler electromagnet includes a single circular wobbler method in which a beam spot having approximately 10 centimeters is rotated along a circular path at about 50 Hz so as to form a uniform dose distribution in the center and a method for forming a uniform dose distribution in the center by scanning a beam spot having the diameter approximately 0.5 to 2 centimeters at a high speed in accordance with a complicated scanning pattern. According to this method, a thin beam spot is scanned with a fixed periodic pattern so as to form a uniform lateral dose distribution. Therefore, this method is also referred as a uniform scanning. As a scanning pattern, a spiral pattern and a saw wave pattern are well known. In a case where a scanning pattern is spiral, a method is called as a spiral wobbler method.

PRIOR ART DOCUMENT

Patent Document

Patent Document 1: Japanese Patent Application Laid-Open No. 2002-191709

Non-Patent Document

Non-Patent Document 1 Masataka Komori, et al, "Optimization of spiral-Wobbler System for Heavy-Ion Radiotherapy", "Japanese Journal of Applied Physics", 2004, Vol. 43, No. 9A, pp. 6463-6467

DISCLOSURE OF THE INVENTION

Problems to be Solved by the Invention

According to the particle beam irradiation apparatus disclosed in Non-patent Document 1 or Patent Document 1, a spiral wobbler method is used. Therefore, in comparison with a single circular wobbler method, a beam spot is scanned with a more complicated scanning pattern. Consequently, it becomes more complicated to check a spiral wobbler system whether the system operates normally or not during irradiation. An objective of the present invention is to provide a particle beam irradiation apparatus which, with a simple structure, is capable of checking the operation of a scanning mechanism and which has a relatively high reliability, in a particle beam irradiation apparatus in which a lateral irradiation field is formed by scanning a particle beam with a wobbler system or other scanning mechanisms.

Means for Solving the Problems

The particle beam irradiation apparatus according to the present invention is provided with a particle beam shielding member for shielding a portion of a scanned particle beam, a prompt signal detector for detecting a prompt signal that is generated when the particle beam which is scanned collides with the particle beam shielding member, and a signal comparison device which predicts a pattern of generation of the prompt signal that is generated by a pre-determined scanning pattern and obtains the pattern to store thereof as a signal time pattern for comparison, wherein the signal comparison device compares the detection signal time pattern, which is the time pattern of the signal detected by the prompt signal detector when the particle beam was scanned according to the pre-determined scanning pattern and the particle beam was irradiated upon a target, to the stored signal time patter for comparison, so as to detect an anomaly of the particle beam scanning or the particle beam shielding member.

Advantage of the Invention

According to the present invention, a particle beam irradiation apparatus which, with a simple structure, is capable of checking the operation of a scanning mechanism and which has a relatively high reliability can be provided.

EMBODIMENTS FOR CARRYING OUT THE INVENTION

Embodiment 1

Figure 1:
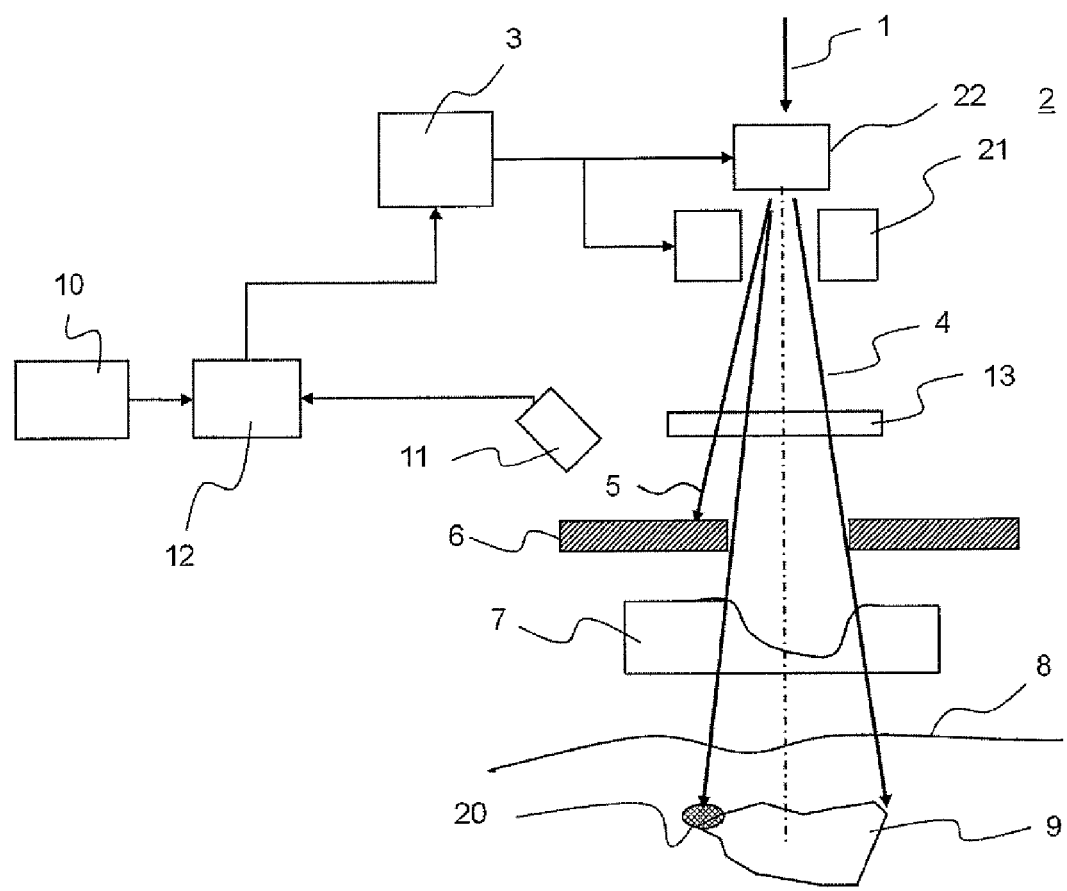
FIG. 1 is a block diagram schematically illustrating the configuration of a particle beam irradiation apparatus according to Embodiment 1 of the present invention.

FIG. 1 is a block diagram schematically illustrating the configuration of a particle beam irradiation apparatus according to Embodiment 1 of the present invention. The configuration and operation of the particle beam irradiation apparatus shown in FIG. 1 will be described below. A particle beam 1 having predetermined beam energy is obtained by a particle beam accelerator (not shown in FIG.). For example, in performing particle beam therapy, a particle beam including a proton beam having approximately 200 MeV or a carbon beam having approximately 400 MeV/u is used. A wobbler electromagnet 2 (generally, comprising an X-direction scanning electromagnet 21 which scans in an X-direction, and a Y-direction scanning electromagnet 22 which scans in a Y-direction) is excited by a scanning power source 3 so as to scan the incident particle beam 1 with a predetermined pattern. The scanning power source 3 is, for example, a pattern power source which generates a spiral pattern or a pattern power source which provides a saw-wave electric current to the wobbler electromagnet 2. The incident particle beam 1 becomes a scanned particle beam 4 by the wobbler electromagnet 2, and a particle beam monitor 13 measures an amount of irradiation and a particle beam position of the particle beam 4. A flat part of a lateral dose distribution which is made by the wobbler electromagnet 2 is cut by a collimator 6 so as to form an irradiation field in accordance with a shape of an affected part (a shape which is viewed from a travelling direction of a particle beam). Among particle beams 4 which are scanned, a particle beam 5 is a particle beam which is scanned and collided with the collimator 6 so as to be shielded. A patient bolus 7, for adjusting the maximum range of a particle beam and conforming a distant stop position of an spread out Bragg peak of a particle beam to the boundary of an affected part 9, is provided at downstream of the collimator 6. Further, a device called ridge filter (not shown in FIG.) is used so as to spread the width of a Bragg peak to be the depth width of an affected part. The particle beam 4 which passes through the patient bolus 7 and the surface of a body of a patient 8 so as to form a beam spot 20 on the affected part 9, and the beam spot 20 is to be scanned by the wobbler electromagnet 2. A prompt radiation detector 11 measuring a prompt radiation (a gamma-ray, a neutron ray, etc.) which is generated when particle beam 5 collides with the collimator 6 is provided. On the other hand, a particle beam irradiation apparatus according to Embodiment 1 of the present invention includes a beam information supply part 10 which supplies information regarding a particle beam which is extracted from an accelerator including time change information of a particle beam electric current which is obtained by an accelerator and on-off timing signal of a particle beam. Further, a signal comparison device 12 which stores a signal time pattern for comparison which is a time pattern of a prompt radiation signal which is calculated beforehand based on a parameter including a wobbler periodical pattern and an opening shape of a collimator device is also included. The signal comparison device 12 compares a detected signal time pattern which is a time pattern of a prompt radiation signal which is detected by a prompt radiation detector 11 to a signal time pattern for comparison.

Figure 2:
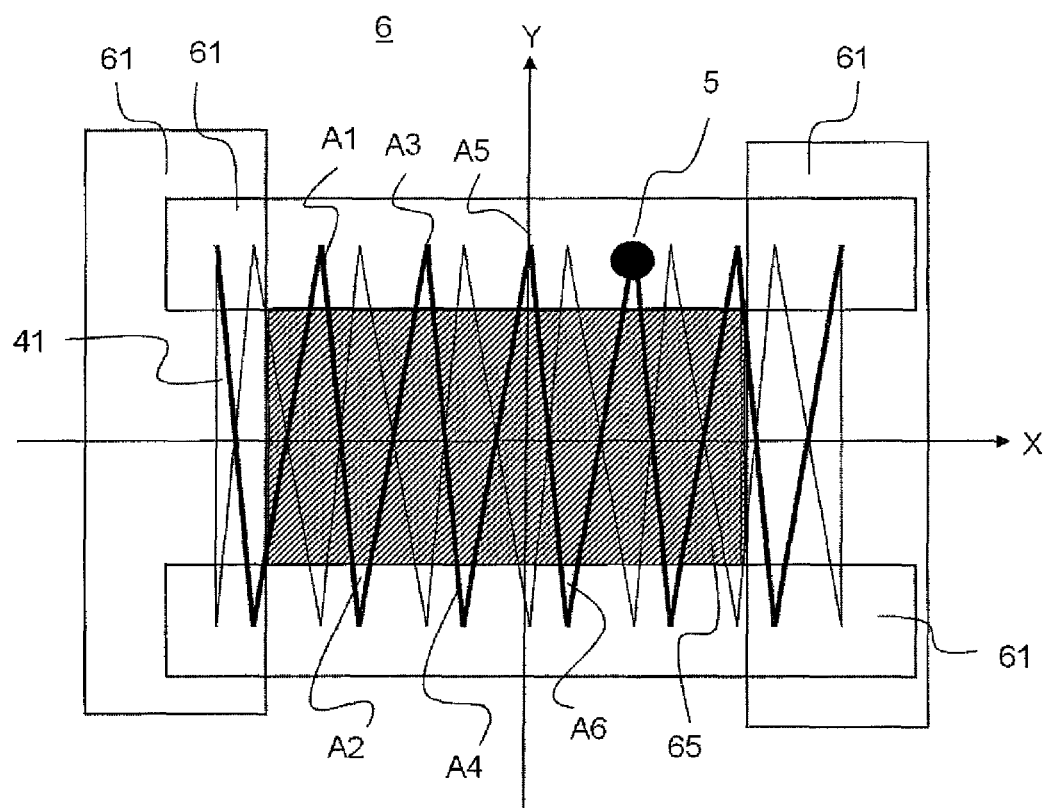
FIG. 2 is a plane view of a collimator of a particle beam irradiation apparatus according to Embodiment 1 of the present invention seen from an incident direction of a particle beam.

FIG. 2 is a plane view of a collimator 6 viewed from an incident direction of a particle beam and shows the position relationship between the collimator 6 and the scanned particle beam 4. The collimator 6 comprises four collimator leaves 61, and by adjusting a position of each collimator leaf 61, an opening region of the collimator 6, that is, a region where the particle beam 4 passes through the collimator 6 is determined. In FIG. 2, a region shown by slanting lines is an opening part 65 of the collimator 6, which is a region where the particle beam 4 passes through the collimator 6. In FIG. 2, X and Y show the axes of coordinates on a plane which is parallel to a collimator plane. Further, A1, A2, A3, A4, A5 and A6 show parts where the scanned particle beam 4 is shielded by the collimator 6 so as to collide with the collimator 6. As above-mentioned, the collimator 6 is a particle beam shielding member. A straight line pattern shown by reference character 41 is an example of a track pattern of a scanned particle beam on a plane of the collimator 6. In FIG. 2, an example in which the track pattern 41 of a particle beam is a saw-wave pattern in an X-direction and a Y-direction is shown.

Next, an operation of a particle beam irradiation apparatus according to Embodiment 1 of the present invention will be described. First, in a therapy plan, an opening shape of a collimator is determined for each patient so as to irradiate only a volume of an affected part with a particle beam. In FIG. 2, for simplicity, the collimator 6 having the simplest configuration is shown, however, practically, in many cases, a collimator which is produced by excavating a plate of metal or an automatic control type multi-leaf collimator in which leaf positions can be changed is used. Further, in a therapy plan, a scanning parameter of a particle beam which is necessary for irradiating an affected part is determined. A scanning parameter includes a scanning pattern to be used, the maximum range of a scanning pattern which may be called a scanning radius, etc. It is necessary to make a uniform irradiation range, which is obtained by scanning a particle beam, bigger than an opening part 65 of the collimator 6. Eventually, only a particle beam which passes through a collimator reaches an affected part, and forms an irradiation field so as to conform to an affected shape.

Next, by using information regarding an opening shape of a collimator including a direction of the collimator 6 which is determined, a scanning pattern of a particle beam and scanning range, a time pattern of a prompt radiation signal, which is estimated to be outputted by detecting a prompt radiation which is generated by colliding the particle beam with the collimator 6 is detected with the prompt radiation detector 11, is calculated. The time pattern of the prompt radiation signal which is obtained by the above-mentioned calculation is a signal time pattern for comparison. Specifically, during the period when a particle beam track completely passes through an opening part of a collimator, a prompt radiation signal is zero. During the period when a particle beam track is shielded by the collimator 6, a prompt radiation signal has a predetermined value. Here, the magnitude of a prompt radiation signal is proportional to a beam current intensity on this occasion, however, in many cases; a particle beam current itself changes with time. Therefore, in performing calculation, first, existence or non-existence of a prompt radiation signal is set to be a parameter. An example in which a collimator is a simple block collimator having four pieces as shown in FIG. 2, and a scanning pattern is a saw-tooth wave as shown in FIG. 2 will be described.

Figure 3:
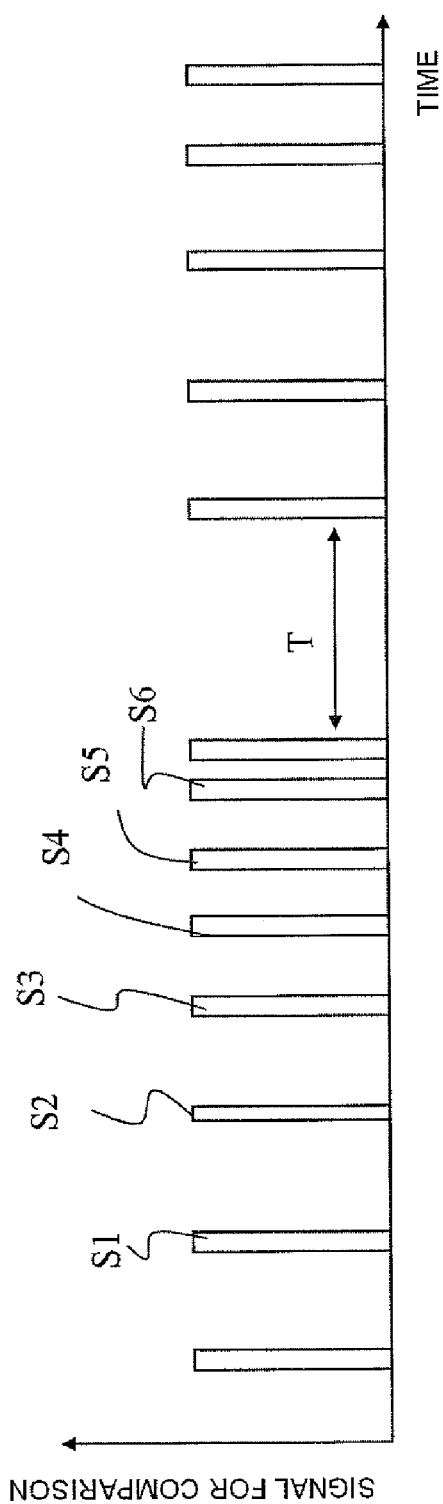
FIG. 3 is a diagrammatic view showing an example of a signal time pattern which is obtained by calculation for comparison of a particle beam irradiation apparatus according to Embodiment 1 of the present invention.

FIG. 3 shows an example of a time pattern of a prompt radiation signal which is obtained by calculation based on information regarding a shape of an opening part 65 of the collimator 6 and a scanning pattern of a particle beam, that is, an example of a signal time pattern for comparison. During the period when the particle beam 4 passes through the opening part 65 of the collimator 6, a prompt radiation which is generated by the collimator 6 is not observed, and during the period when the particle beam 5 is shielded by the collimator 6 (collimator leaf 61), a prompt radiation is detected and a signal is outputted. Further, in a case where a particle beam accelerator is a synchrotron accelerator, a particle beam current becomes the pulsed state, therefore, during a beam-off period shown by T in FIG. 3, a prompt radiation which is generated by the collimator 6 is not observed.

A width of S1 signal shown in FIG. 3 is proportion to a length of a particle beam track in a region A1 shown in FIG. 2. In the same way, the time when a prompt radiation which is generated by the particle beam 5 which is shielded by the collimator 61 and a duration can be predicted by calculation.

Then, a signal time pattern for comparison shown in FIG. 3 is stored in a signal comparison device 12 shown in FIG. 1. Then, a position of the collimator leaf 61 is set so as to be a shape which is determined in a therapy plan, other irradiation equipment and a parameter is adjusted and set beforehand. By performing the above-mentioned, the preparation for start of therapy is ready.

Next, when the scanning power source 3 of the wobbler electromagnet 2 provides an electric current in accordance with a planned scanning pattern, the wobbler electromagnet 2 is excited to correspond to a scanning pattern. Then, a particle beam is extracted from an accelerator so as to be incident on the wobbler electromagnet 2 via a beam transport system. The particle beam 1 which is incident to the wobbler electromagnet 2 is scanned in accordance with a scanning pattern so as to be the particle beam 4. The particle beam 4 passes through the opening part 65 of the collimator 6, the patient bolus 7 and a patient body's surface 8, and after that, the particle beam 4 is irradiated onto an affected part 9.

Figure 4:
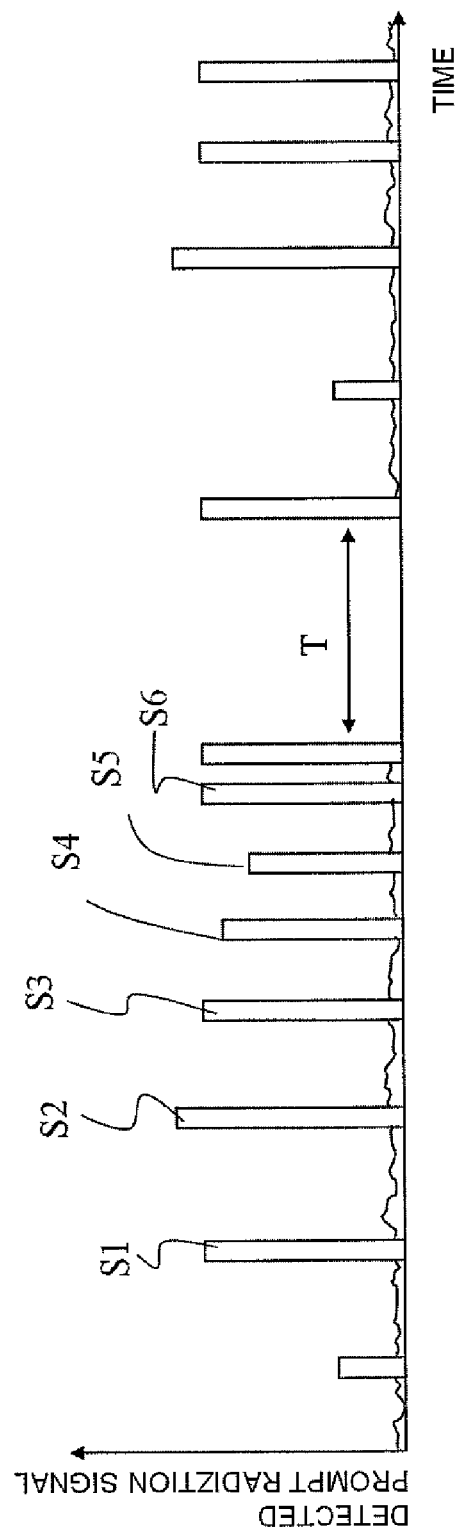
FIG. 4 is a diagrammatic view showing an example of a detected signal time pattern which is detected by a prompt signal detector of a particle beam irradiation apparatus according to Embodiment 1 of the present invention.

On the other hand, the particle beam 5 which is shielded by the collimator 6 collides with the collimator 6, and reacts with atomic nucleus in the collimator so as to generate a prompt radiation such as a prompt γ-ray instantly. Since a prompt radiation is generated in a moment when the particle beam 5 collides with the collimator 6, the generation timing is determined uniquely by the track pattern 41 of the particle beam 4 on a surface of a collimator and a shape of the opening part 65 of the collimator 6. The prompt radiation detector 11 detects a prompt radiation which is generated by the collimator 6. FIG. 4 shows an example of a prompt radiation signal which is detected by the prompt radiation detector 11, that is, a detected signal time pattern. In FIG. 4, S1, S2, S3, S4, S5 and S6 are prompt radiation signals which are generated from a part corresponding to A1, A2, A3, A4, A5 and A6, respectively. Further, for example, when a particle beam irradiates the affected part 9, a prompt radiation is generated also in the affected part 9; however, the intensity of the prompt radiation is extremely weak in comparison with the intensity of the prompt radiation which is generated by the collimator 6. In FIG. 4, a signal such as a weak noise is a signal showing such that a prompt radiation which is generated in the affect part 9 is detected by the prompt radiation detector 11, and it can be easily discriminated whether the detected prompt radiation is a prompt radiation which is generated by the collimator 6 or not.

The detected signal time pattern is transmitted to the signal comparison device 12. The signal comparison device 12 checks the detected signal time pattern against a signal time pattern for comparison which is stored so as to monitor such that a scanning pattern is the one as it was planned or not. For example, in a case where a scanning pattern is periodical, in a period when a particle beam is ON (a period when a particle beam is extracted from an accelerator), in a case where the maximum time distance of adjacent signals in a signal time pattern for comparison is set to be $\Delta T$, in a case where a time distance of adjacent signals in a detected signal time pattern is longer than $\Delta T$, it can be judged such that any abnormality is generated in a scanning mechanism of a particle beam.

As can be easily recognized by FIG. 2, basically, $\Delta T$ is determined by the maximum opening of the opening part 65 of the collimator 6 and a detailed shape of a scanning pattern, therefore, when a time interval of adjacent prompt radiation signal pulses is longer than $\Delta T$, it is suggested such that a range of a particle beam track is changed to be an inside of the opening part 65. Further, during irradiation, in a case where the opening part 65 of the collimator 6 is fluctuated, a pattern of a detected signal time pattern (a time width of a pulse, or interval of pulses) of a prompt radiation which is detected by the prompt radiation detector 11 is also changed. Consequently, also in a case where an abnormality is generated in a collimator during irradiation, the signal comparison device 12 can detect the abnormality. In a case where a scanning period of a periodic scanning pattern which is used in a particle beam irradiation apparatus is approximately 20 Hz to 60 Hz, a time interval of a signal pulse ΔT is approximately 25 msec to 8.3 msec. A response time of the prompt radiation detector 11 is approximately 10 μsec, and is sufficiently fast in comparison with ΔT, therefore, the timing when a particle beam passes through a collimator edge can be detected with sufficiently good accuracy.

Figure 5:
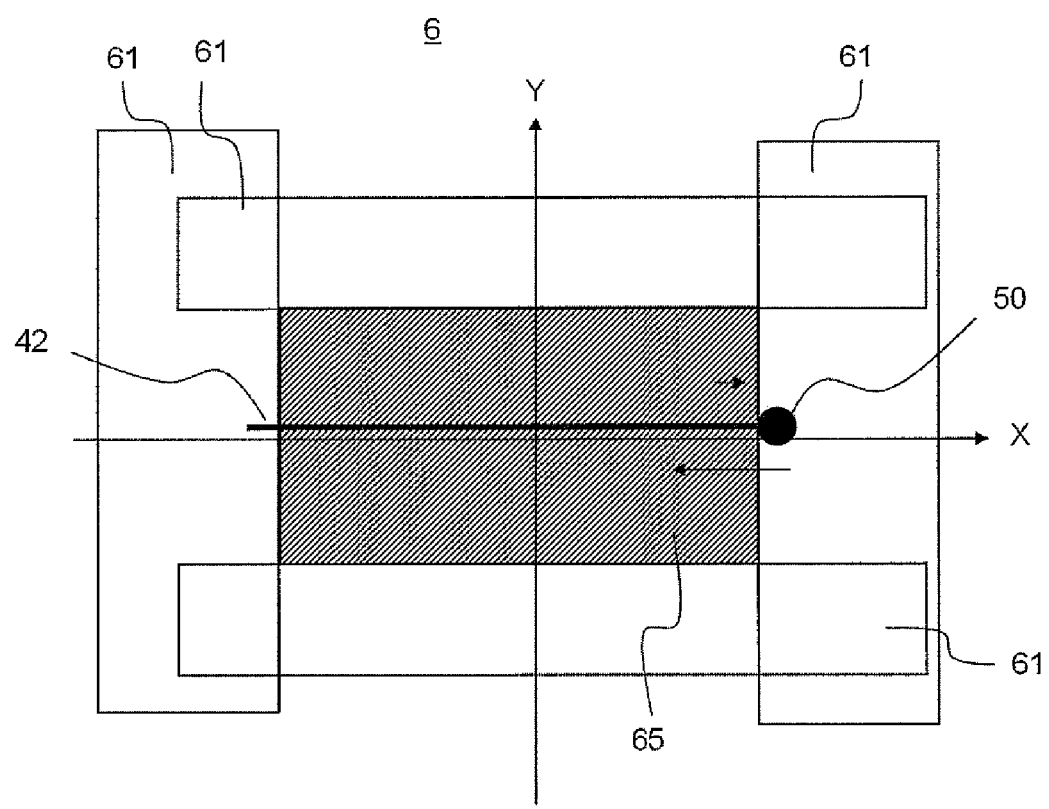
FIG. 5 is a plane view of a collimator viewed from an incident direction of a particle beam in a case where an abnormality is generated in a particle beam irradiation apparatus according to Embodiment 1 of the present invention.
Figure 6:
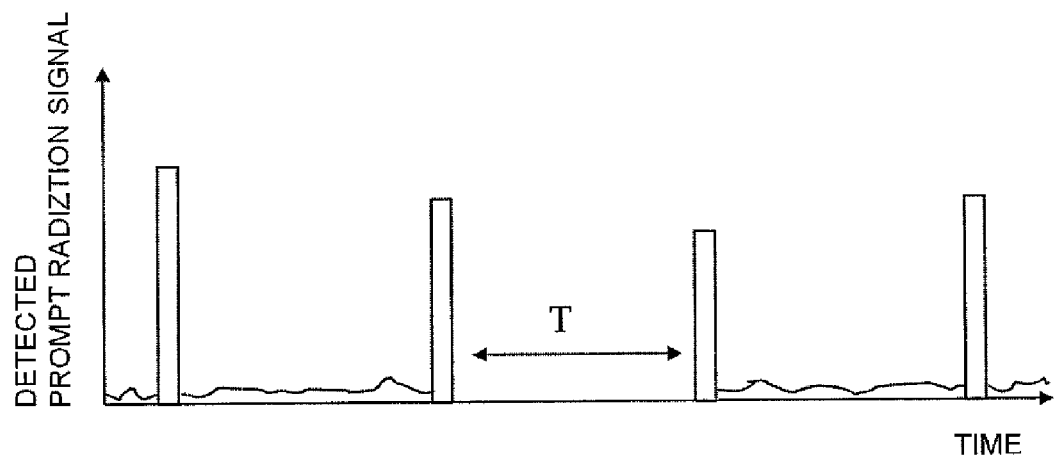
FIG. 6 is a diagrammatic view showing an example of a detected signal time pattern which is detected by a prompt signal detector in a case where an abnormality shown in FIG. 5 is generated in a particle beam irradiation apparatus according to Embodiment 1 of the present invention.

FIG. 5 shows schematically a case in which an abnormality in a scanning pattern of a particle beam is observed, an amount of scanning in a Y-direction is zero, and a particle beam track 42 is linear along an X-direction. FIG. 6 shows a detected signal time pattern of a prompt radiation which is detected by the prompt radiation detector 11 corresponding to FIG. 5. A strong prompt radiation is observed only during a period when a particle beam is shielded by the collimator 6 at both ends (for example, a particle beam position 50). The difference between a detected signal time pattern shown in FIG. 6 and a signal time pattern for comparison shown in FIG. 3 is clear, therefore an abnormality can be easily judged by the signal comparison device 12.

Figure 7:
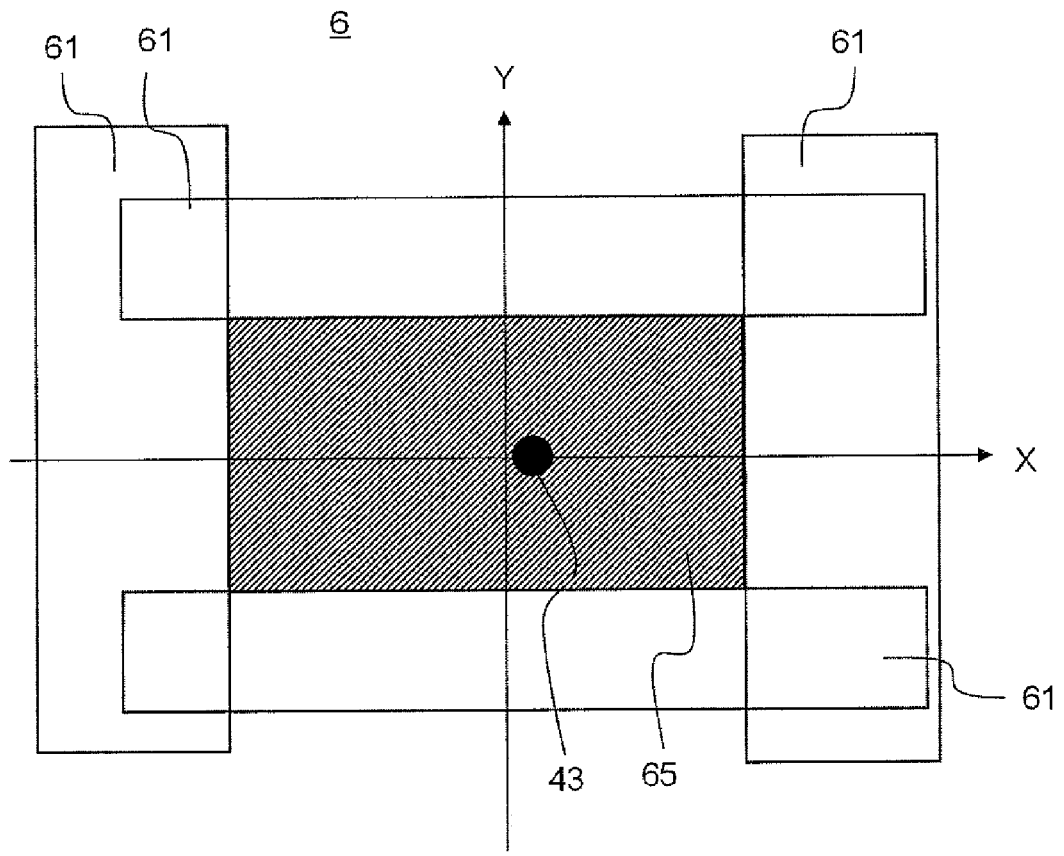
FIG. 7 is a plane view showing a collimator viewed from an incident direction of a particle beam in a case where another abnormality is generated in a particle beam irradiation apparatus according to Embodiment 1 of the present invention.
Figure 8:
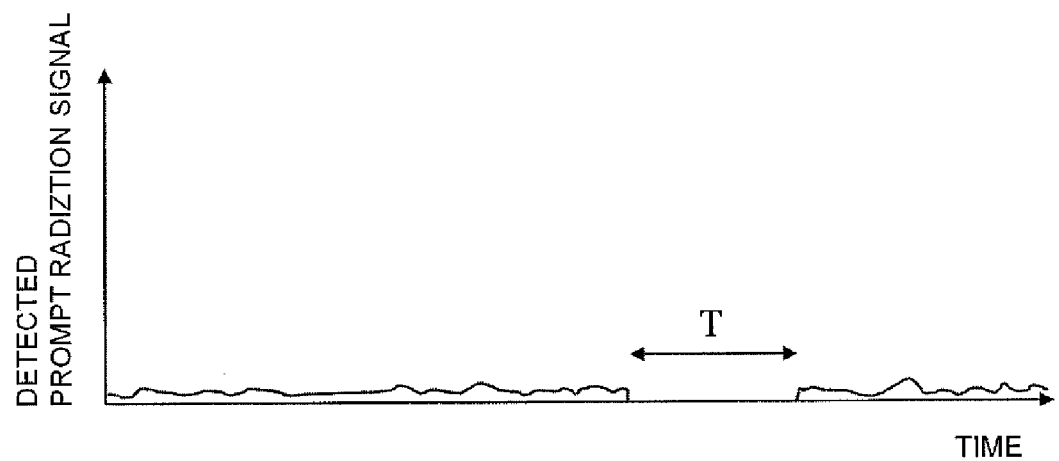
FIG. 8 is a diagrammatic view showing an example of a detected signal time pattern which is detected by a prompt signal detector in a case where an abnormality shown in FIG. 7 is generated in a particle beam irradiation apparatus according to Embodiment 1 of the present invention.
Figure 9:
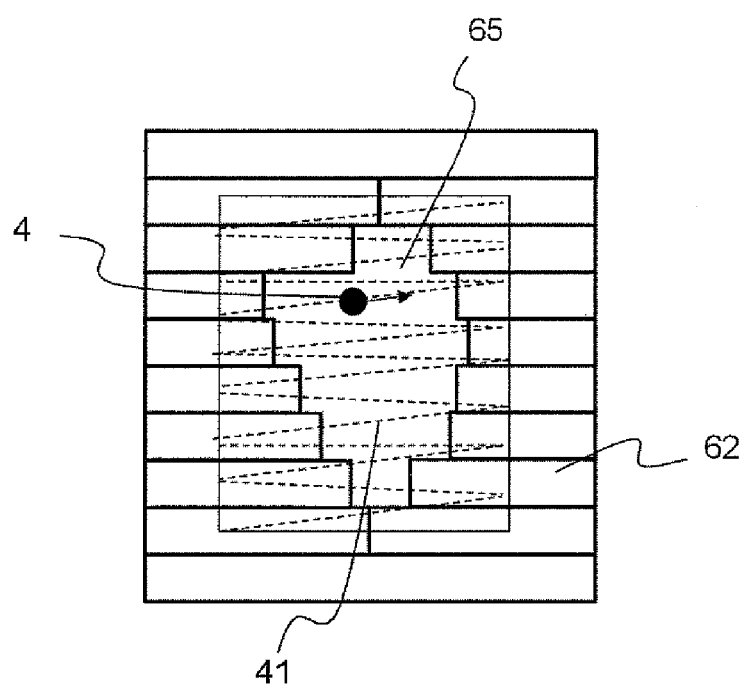
FIG. 9 is a plane view of another collimator of a particle beam irradiation apparatus according to Embodiment 1 of the present invention viewed from an incident direction of a particle beam.

FIG. 7 shows an example of the relationship of a position of a particle beam 51 and the opening part 65 of a collimator when an abnormality is generated in the wobbler electromagnet 2, and a scanning of a particle beam is completely stopped. FIG. 8 shows a detected signal time pattern of a prompt radiation which is detected by the prompt radiation detector 11 corresponding to FIG. 7. In a case where a scanning of a particle beam is stopped and a position of a particle beam 43 is a position shown in FIG. 7, as shown in FIG. 8, a prompt radiation signal which is generated by the collimator 6 can not be observed by the prompt radiation detector 11. Therefore, an abnormality of a scanning pattern can be detected by comparing a detected signal time pattern to a signal time pattern for comparison with the signal comparison device 12.

As above-mentioned, by a particle beam irradiation apparatus according to Embodiment 1 of the present invention, in addition to abnormality monitoring function of conventional wobbler scanning power sources and abnormality monitoring function of particle beam monitors, abnormality of a scanning pattern can be detected by a simple system configuration, therefore, further improvement of reliability of a particle beam irradiation apparatus can be obtained.

Further, the present invention has an effect such that an abnormality of the collimator 6 can be detected. Further, in the above, a case in which the collimator 6 comprises four pieces of collimator leaf 61 was described; however, the configuration is not limited thereto. It is needless to say such that a case of a multi-leaf collimator in which the opening part 65 is formed by using many collimator leaves 62 can produce an effect of the present invention.

Further, in FIG. 1, a case in which the prompt radiation detector 11 is arranged at an upstream side of the collimator 6 is shown, however, even in a case where the prompt radiation detector 11 is arranged at a downstream side of the collimator 6, the effect is the same. In a case where the prompt radiation detector 11 is arranged at a downstream of a treatment table, there is an effect such that a prompt γ ray or a prompt neutron ray which is generated by a nucleus reaction which is generated in a collimator can be effectively detected.

Further, in the above, a case in which a particle beam scanning pattern is a saw-wave pattern is described; however, a pattern is not limited thereto. Even in a case where a scanning pattern is a spiral scanning pattern which is described in Patent Document 1 or Non-Patent Document 1, the same effect can be obtained.

Further, in the above, a case in which Bragg peak of a particle beam is spread to a width of a depth direction of an affected part by using a ridge filter was described, however even in a case where a therapy system, in which irradiation is performed by using an spread out Bragg peak having a narrow width such as a stacked conformation irradiation system in which an affected part is divided into a plurality of sliced areas along a depth direction, and an energy of a particle beam is changed for each slice so as to irradiate the slice, is used, the effect of the present invention is the same.

Further, in the above, a case in which a particle beam is obtained by a synchrotron accelerator is described, however, even in a case where a particle beam irradiation apparatus in which a cyclotron accelerator is used, the same effect can be obtained.

Further, in the above description, the prompt radiation detector 11 is described as a detector which detects a prompt radiation signal, however, even when the prompt radiation detector 11 comprises a detector which detects all or a part of a prompt signal including a gamma ray or a neutron signal, among a prompt signal which is generated when a particle beam collides with the collimator 6 comprising a brass, an iron, etc., an effect which is described in the above is basically same. It is important to detect a signal which is generated promptly after a particle beam collides with a collimator, and compare the detected signal time pattern to a signal time pattern for comparison which is obtained by calculation. This is because such that the time pattern of the prompt signal is determined by an opening shape of the collimator 6, a rotation angle against its beam irradiation direction, a scanning track of the particle beam 4, 5, and time information regarding intensity of the particle beam.

Further, a case in which special material is coated with or is added to the collimator 6 so as to allow signals to easily generate when the particle beam 5 collides with the collimator 6, and then the signals are detected; an effect of the present invention can be obtained. Signals may include, for example, a sound wave signal, a visible light signal, invisible light signal and a secondary electron signal. In the present invention, a signal which is generated when the particle beam 5 collides with the collimator 6 (particle beam shielding member) is defined as a prompt signal, for example, a signal radiation ray such as a gamma ray and a neutron ray, a secondary electron, a sound wave, a light, etc. When the prompt radiation detector 11 is set to be the prompt signal detector 11 which detects a prompt signal to be detected, the above-mentioned effect can be obtained in the same way.

Further, according to the present invention, in a case where a collimator is multi leaf collimator, a time pattern for comparison of a prompt signal is made based on a shape of a multi-leaf collimator whose opening shape is different for each patient, in addition to monitoring of operation of a spiral wobbler system during irradiation, a case in which a shape of a multi-leaf collimator is fluctuated during irradiation can also be detected.

Further, according to the present invention, a time pattern of a prompt signal which is generated promptly when a particle beam collides with a collimator is monitored, therefore, the prompt signal can be detected almost at the same time when the particle beam collides with the collimator. Consequently, because of no time-delay, the timing when a particle beam collides with a collimator can be detected with excellent accuracy.

Further, according to the present invention, by detecting a prompt signal such as a gamma ray or light which is generated by colliding a particle beam with a collimator, the timing when a particle beam collides with is detected, therefore, even in a case of a beam current of several nano ampere (nA=1.0E−9 A) which is used in particle beam therapy, the timing when a particle beam collides with a collimator with excellent accuracy can be detected without the need for special remodeling for example, insulating a collimator body. The above-mentioned has an effect to avoid the complication of a collimator which is used in a particle beam irradiation apparatus. That is, a collimator such as a multi-leaf collimator which is provided at an irradiation nozzle in the way as it was, and an effect of the present invention can be obtained. Further, in a case a prompt signal is a signal of a prompt radiation ray such as a prompt gamma ray, even when the prompt radiation detector 11 is provided at a position which is far from a collimator, for example, across a treatment table, or an opposite side of an irradiation nozzle, a prompt radiation signal which is generated by a collimator can be detected.

Embodiment 2

Figure 10:
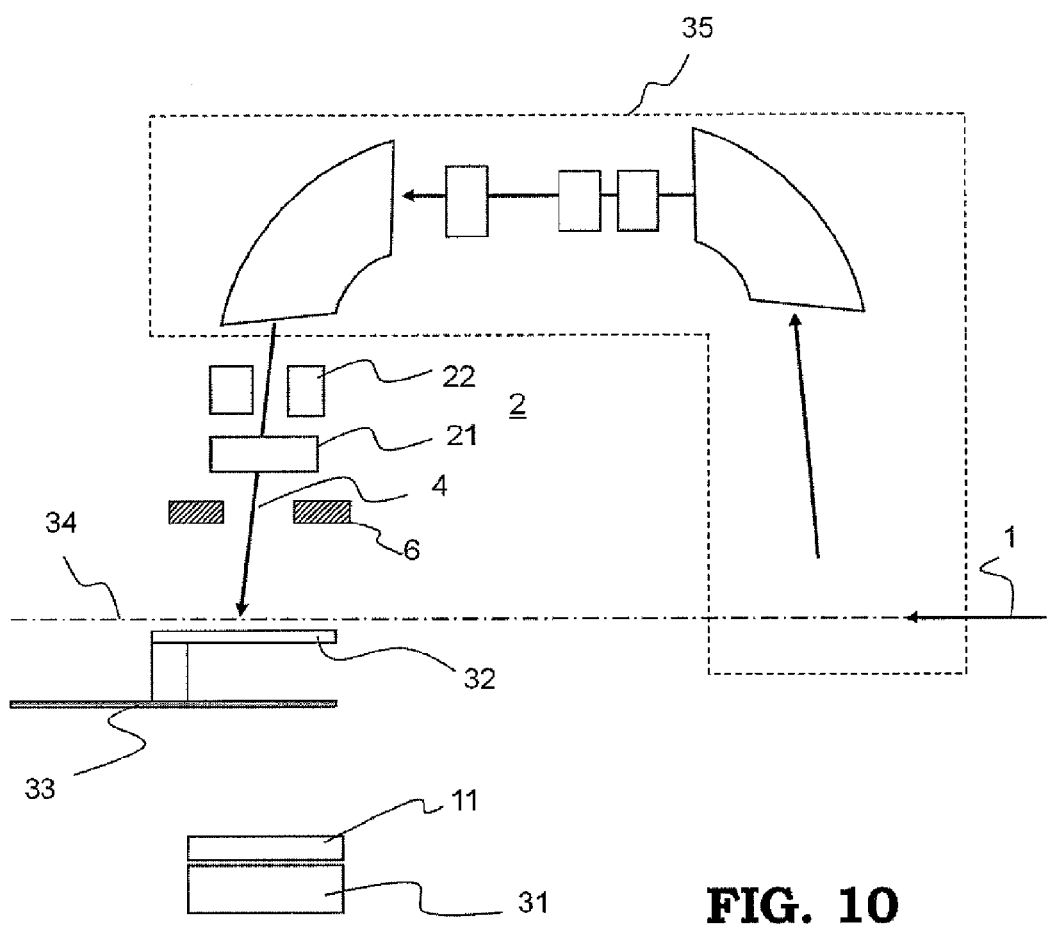
FIG. 10 is a block diagram schematically illustrating the configuration of a particle beam irradiation apparatus according to Embodiment 2 of the present invention.

FIG. 10 is a block diagram schematically illustrating the configuration of a particle beam irradiation apparatus according to Embodiment 2 of the present invention. In FIG. 10, a reference character which is same as that in FIG. 1 shows a same or a corresponding part. In Embodiment 2, a particle beam irradiation apparatus having a rotating gantry mechanism is applied to the present invention. A particle beam irradiation apparatus shown in FIG. 10 includes a counter weight 31 for reducing a rotating torque of a rotating gantry, a treatment table 32, a treatment room floor 33, a rotating shaft 34 of a rotating gantry and rotating gantry electromagnets 35 which transport a particle beam so as to constitute a rotating gantry.

In Embodiment 2, the prompt radiation detector 11 is provided at a rotating flame together with the counter weight 31. Except for the above-mentioned configuration, the configuration of Embodiment 2 is same as that of Embodiment 1. Therefore, basic operation of Embodiment 2 is same as that of Embodiment 1. In Embodiment 2, the prompt radiation detector 11 is provided at a rotating flame together with the counter weight 31 of the rotating gantry 31, therefore, concentrated component in front direction of a prompt radiation signal (including a gamma ray, a neutron ray, etc.) which is generated from the collimator 6 can be constantly collected regardless of rotating degree of a rotating gantry. Consequently, at any irradiation angle of a rotating gantry, a prompt radiation signal having an excellent signal-to-noise ratio can be detected.

Embodiment 3

Figure 11:
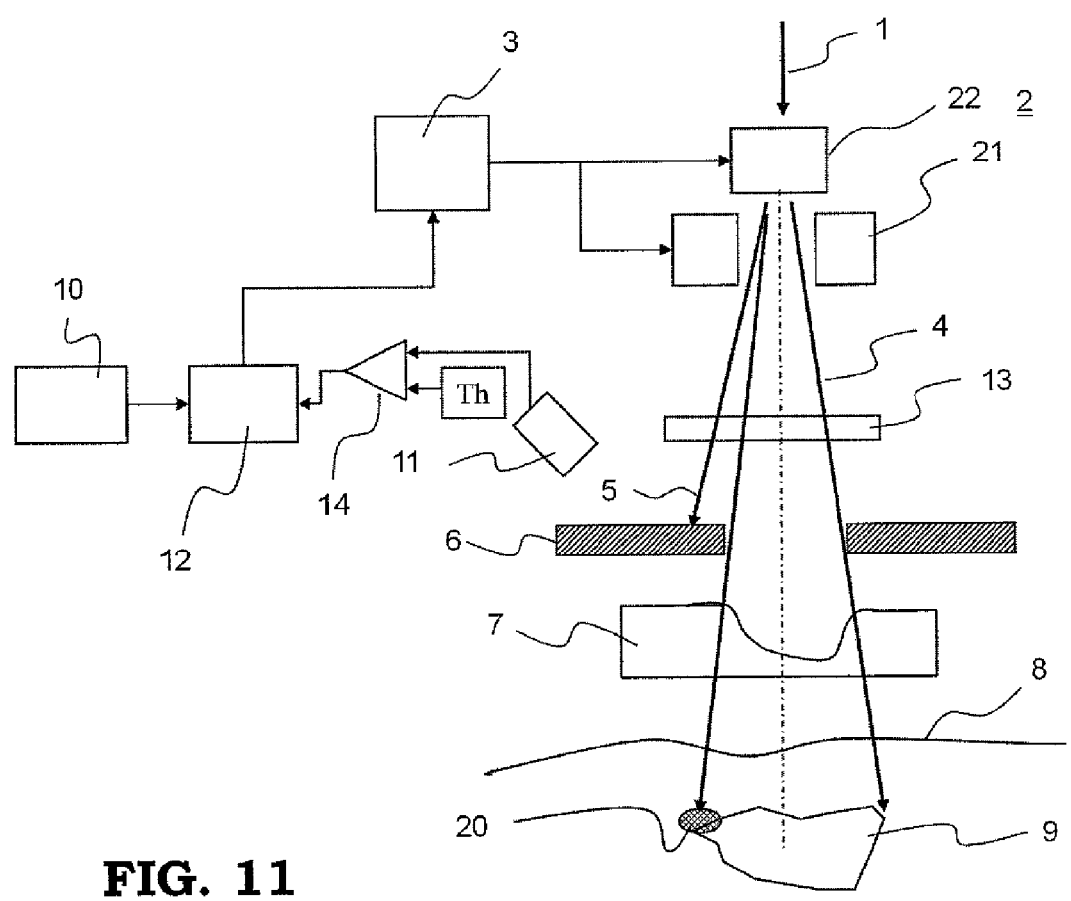
FIG. 11 is a block diagram schematically illustrating the configuration of a particle beam irradiation apparatus according to Embodiment 3 of the present invention.
Figure 12:
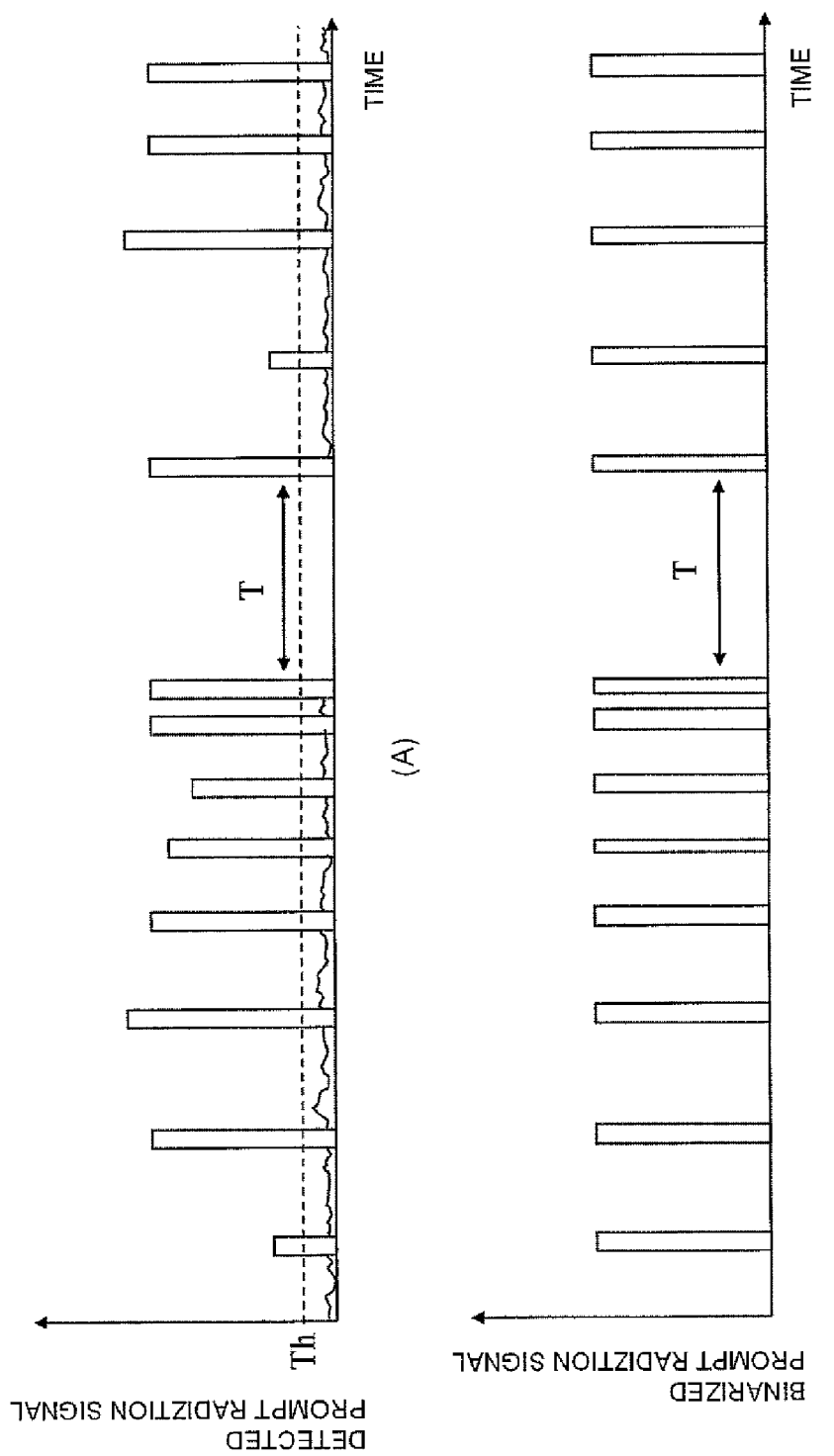
FIG. 12 is a diagrammatic view showing an example of a detected signal time pattern which is detected by a prompt signal detector of a particle beam irradiation apparatus according to Embodiment 3 of the present invention.

FIG. 11 is a block diagram schematically illustrating the configuration of a particle beam irradiation apparatus according to Embodiment 3 of the present invention. In FIG. 11, a reference character which is same as that in FIG. 1 shows a same or a corresponding part. In Embodiment 3, a prompt radiation signal which is detected by the prompt radiation detector 11 is converted into a signal having a constant height through a comparator 14 which is a circuit which compares the detected prompt radiation to a predetermined threshold value Th that is, a prompt radiation signal is binarized. A pattern shown in FIG. 12 (A) is a prompt radiation signal itself which is measured by the prompt radiation detector 11 shown in FIG. 3. In a case where a signal having a level larger than a level shown by Th in FIG. 12 (A) in regard to this prompt radiation signal is measured, the processing to produce an output is performed. In a case where a comparator 14 is a general comparator, when a signal shown in FIG. 12 (A) is inputted to an input terminal of a comparator 14 and a level corresponding to Th is set as a comparing level of the comparator 14, an output which is binarized as shown in FIG. 12 (B) is obtained as an output of the comparator. A prompt radiation of a detected prompt radiation signal having a level lower than a threshold value is a prompt radiation other than a prompt radiation which is generated by the collimator 6, for example, a prompt radiation which is generated in an affected part which is an irradiation object, the processing which can eliminate a prompt radiation having the above-mentioned level from a detecting object can be performed.

According to Embodiment 3, whether a particle beam collides with the collimator 6 or not can be judged by existence or non-existence of a prompt radiation signal which is treated, consequently, detected signal time pattern can be grasped more easily, and the detected signal time pattern can be compared easily to a signal time pattern for comparison. Consequently, an operation of irradiation system during irradiation can be monitored easily.

Embodiment 4

Figure 13:
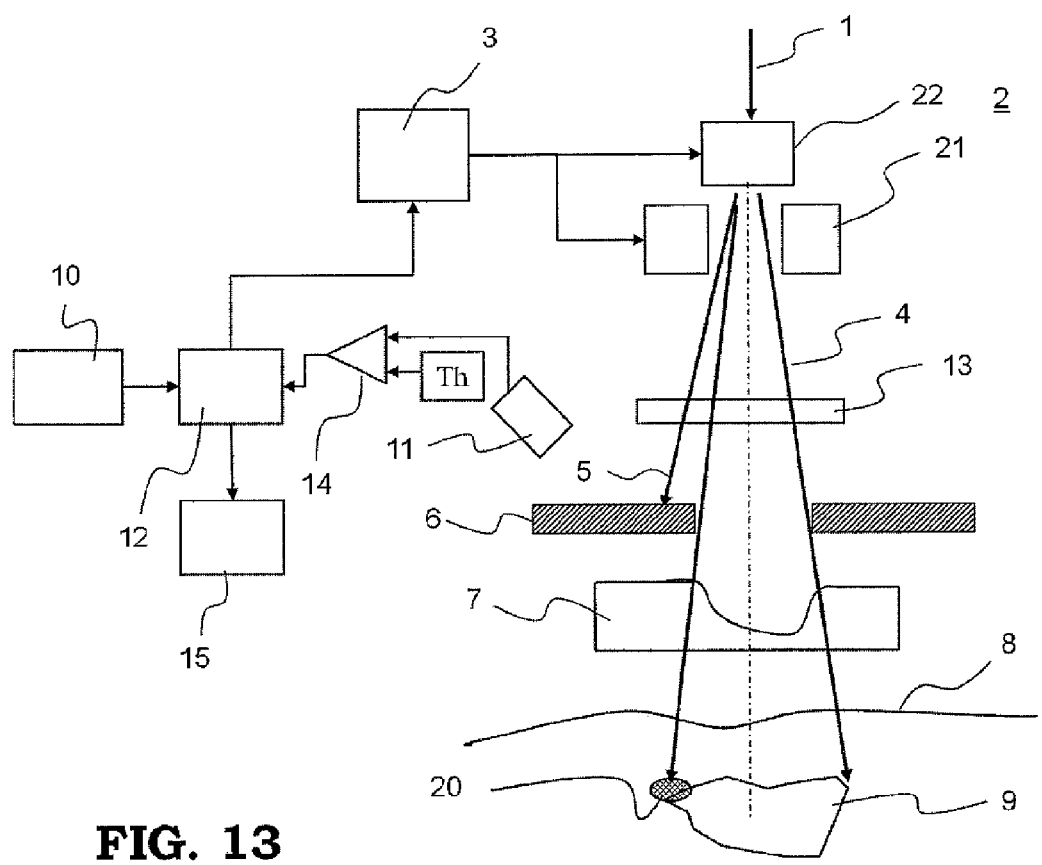
FIG. 13 is a block diagram schematically illustrating the configuration of a particle beam irradiation apparatus according to Embodiment 4 of the present invention.
Figure 14:
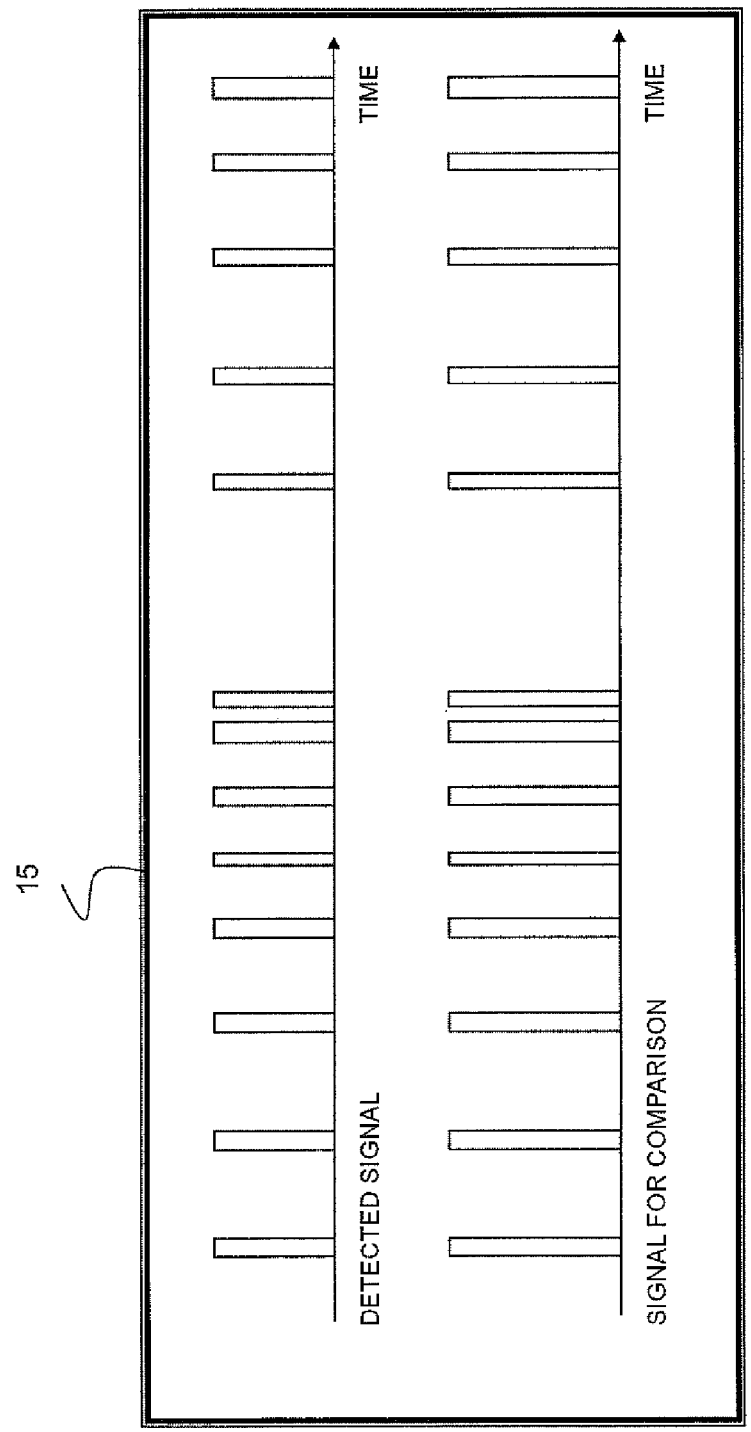
FIG. 14 is an image diagram showing an example of a screen of a display system of a particle beam irradiation apparatus according to Embodiment 4 of the present invention and FIG. 15 is an image diagram showing a main section of a particle beam irradiation apparatus according to Embodiment 5 of the present invention.

FIG. 13 is a block diagram schematically illustrating the configuration of a particle beam irradiation apparatus according to Embodiment 4 of the present invention. In FIG. 13, a reference character which is same as that in FIG. 11 shows a same or a corresponding part. In FIG. 13, reference numeral 15 shows a display apparatus, for example, a detected signal time pattern and a signal time pattern for comparison are displayed in the display apparatus 15. FIG. 14 shows an image of a screen which is shown by the display apparatus 15. In Embodiment 4, by displaying a detected signal time pattern which is measured during irradiation in the display apparatus 15 which is provided in a treatment room, an operation room, etc., during irradiation, an operation of a particle beam irradiation apparatus can be monitored intuitively. Further, by displaying a signal time pattern for comparison which is obtained by calculation based on a shape of a collimator which is used during irradiation, a rotating degree position, a scanning pattern of a particle beam, a particle beam current time information in the display apparatus 15 together with a detected signal time pattern, during irradiation, an operation of a particle beam irradiation system can be monitored more easily. In FIG. 14, an example in which a detected signal time pattern is displayed in an upper stage and a signal time pattern for comparison is displayed in a lower stage is shown, however, it is not limited thereto, and both of them may be superimposed and displayed, or the difference between them may be displayed.

Embodiment 5

Figure 15:
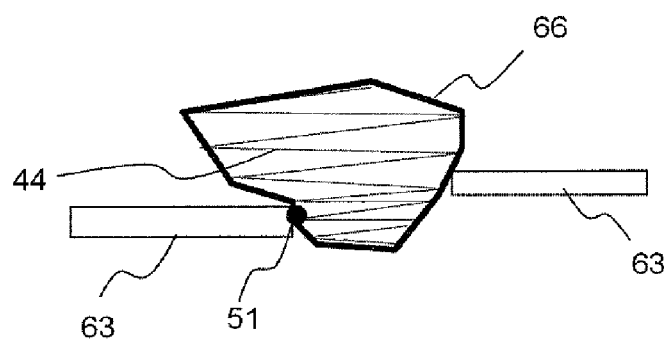

FIG. 15 is an image diagram showing a main section of a particle beam irradiation apparatus according to Embodiment 5 of the present invention. FIG. 15 is a diagram showing a track of a particle beam at a position corresponding to FIG. 2 in Embodiment 1. In a particle beam irradiation apparatus, there is an irradiation method by which a lateral irradiation field is formed by a particle beam itself without using a collimator such as a step scan irradiation method in which a lateral irradiation field is formed only by a scanning electromagnet which scans a particle beam. In this case, there is no collimator, therefore, there is no object with a particle beam collides so as to generate a prompt signal. Consequently, a prompt signal which is described in Embodiments 1 to 4 can not be obtained. Therefore, in a particle beam irradiation apparatus in Embodiment 5, in the configuration without using a collimator, at least one particle beam shielding member, which shields a small part of a particle beam so as to generate a prompt signal, to an extent not much as to exert an influence on an irradiation field forming, is provided at a downstream of a scanning electromagnet. That is, as shown in FIG. 15, a particle beam shielding member 63 is provided at a position where only a part of a particle beam collides with as shown by a particle beam 51 in the boundary of a scanning region 66 which is formed by a track of a particle beam 44 which is scanned. Based on a scanning pattern and timing information such as a scanning start time, the time when a particle beam collides with the particle beam shielding member 63 can be predicted beforehand and can be calculated. A prompt signal of a prompt gamma ray which is generated in the particle beam shielding member 63, which is predicted is stored in a signal comparison device 12 as a signal time pattern for comparison. This signal time pattern for comparison is compared to a detected signal time pattern which is detected by a prompt signal detector 11 during irradiation, and cross check of soundness of irradiation system can be performed.

As above-mentioned, the present invention can be applied to whole of particle beam irradiation apparatuses in which a particle beam is scanned not only by a wobbler system but also by a scanning pattern which is determined beforehand.

REMARKS

1: particle beam
2: wobbler electromagnet
4: particle beam which is scanned
5: particle beam which is shielded by a collimator
6: collimator (particle beam shielding member)
11: prompt radiation detector (prompt signal detector)
12: signal comparison device
14: comparator
15: display apparatus
21: X-direction scanning electromagnet 21
22: Y-direction scanning electromagnet
41: track pattern of a particle beam on a surface of a collimator 6
61, 62: collimator leaf
63: particle beam shielding member
65: opening part of a collimator

The invention claimed is:

1. A particle beam irradiation apparatus in which an incident particle beam is scanned so as to irradiate the particle beam on a target comprising:

a particle beam shielding member configured to shield a part of a scanned particle beam;

a prompt signal detector configured to detect a prompt signal, said prompt signal being generated when the scanned particle beam collides with the shielding member; and a signal comparison device configured to (1) predict a pattern of generation of a prompt signal having been generated by a pre-determined scanning pattern and (2) obtain the predicted pattern to store thereof as a signal time pattern for comparison, wherein the signal comparison device compares the detected signal time pattern, which is the time pattern of the signal detected by the prompt signal detector when the particle beam is scanned according to the pre-determined scanning pattern and the particle beam is irradiated upon a target, to the stored predicted signal time pattern for comparison, so as to detect an anomaly of the particle beam scanning or that of the particle beam shielding member.

2. The particle beam irradiation apparatus according to claim 1, wherein the particle beam shielding member is a collimator for forming a lateral irradiation field of the particle beam in the target.

3. The particle beam irradiation apparatus according to claim 1, wherein the particle beam is scanned and a lateral irradiation field is formed on the target by the particle beam itself, and the particle beam shielding member is provided in at least one part in the boundary of a scanning region of the particle beam.

4. The particle beam irradiation apparatus according to claim 1, wherein the particle beam shielding member is a prompt radiation signal to be generated.

5. The particle beam irradiation apparatus according to claim 4, wherein the prompt signal detector is provided at the downstream of the particle beam than the particle beam shielding member.

6. The particle beam irradiation apparatus according to claim 5, wherein a rotating gantry mechanism having a counter weight is included, and the prompt signal detector is provided so as to move integrally with the counter weight.

7. The particle beam irradiation apparatus according to claim 1, wherein a display for displaying both of the detected signal time pattern and the signal time pattern for comparison or a display for displaying the difference between the detected signal time pattern and the signal time pattern for comparison is provided.

8. A particle beam therapy system in which the particle beam irradiation apparatus according to claim 1 is provided.

* * * * *